United States Patent [19]

Asmar et al.

[11] Patent Number: 4,469,107
[45] Date of Patent: Sep. 4, 1984

[54] AUTOMATIC BLOOD PRESSURE MEASUREMENT DEVICE WITH THRESHOLD COMPENSATION CIRCUITRY AND METHOD FOR PERFORMING THE SAME

[76] Inventors: Raymond A. Asmar, 1 Fairmont Dr., Danbury, Conn. 06810; John Canavan, Bee Brook Rd., Washington Depot, Conn. 06794

[21] Appl. No.: 269,511

[22] Filed: Jun. 1, 1981

Related U.S. Application Data

[63] Continuation-in-part of Ser. No. 9,377, Jan. 2, 1979, abandoned.

[51] Int. Cl.³ .............................................. A61B 5/02
[52] U.S. Cl. .................................................. 128/681
[58] Field of Search ................................ 128/680–683

[56] References Cited

U.S. PATENT DOCUMENTS

| | | | |
|---|---|---|---|
| 3,308,811 | 3/1967 | Gillette et al. | 128/680 |
| 3,349,763 | 10/1967 | Celments, Jr. et al. | 128/660 |
| 3,391,691 | 7/1968 | Young | 128/678 |
| 3,742,937 | 7/1973 | Manuel et al. | 128/690 |
| 3,807,388 | 4/1974 | Orr et al. | 128/690 |
| 3,838,684 | 10/1974 | Manuel | 128/690 |
| 3,903,873 | 9/1975 | Royal et al. | 128/690 |
| 3,908,639 | 9/1975 | McIntyre | 128/672 |
| 3,937,004 | 2/1976 | Natori et al. | 128/672 |
| 3,972,320 | 8/1976 | Kalman | 128/690 |
| 3,978,848 | 9/1976 | Yen et al. | 128/681 |
| 4,009,708 | 3/1977 | Fay, Jr. | 128/690 |
| 4,030,484 | 6/1977 | Kuska et al. | 128/672 |
| 4,052,979 | 10/1977 | Scherr et al. | 128/690 |
| 4,058,118 | 11/1977 | Stupay et al. | 128/690 |
| 4,063,551 | 12/1977 | Sweeney | 128/690 |
| 4,078,551 | 3/1978 | Wohltjen et al. | 128/681 |
| 4,154,238 | 5/1979 | Link | 128/681 |
| 4,261,368 | 4/1981 | Danna et al. | 128/660 |

OTHER PUBLICATIONS

Looney, J., "Blood Pressure by Oscillometry", *Med. Electronics*, Apr. 1978, pp. 57–63.
Fiegel, L. J., "Blood Pressure Measuring", *IBM Tech. Disclosure Bulletin*, vol. 8, No. 6, Nov. 1965.

*Primary Examiner*—Kyle L. Howell
*Assistant Examiner*—Francis J. Jaworski
*Attorney, Agent, or Firm*—Mattern, Ware, Stoltz & Fressola

[57] ABSTRACT

A blood pressure measurement apparatus comprises electronic circuitry which converts an output from a pressure transducer into a digital display for both the systolic and diastolic blood pressure of an individual. The output of the pressure transducer contains an electrical DC voltage component with a superimposed AC voltage component during arterial blood flow. Sample and hold and logarithmic scaling circuits are used to properly sense the AC voltage over a wide range of values so as to eliminate improper sensing due to noise. A digital output display shows the individual's systolic blood pressure while another display shows the current transducer reading which becomes set upon reaching the diastolic pressure. Control circuitry is used to sense occurrence of the systolic and diastolic pressures.

In one embodiment, the circuitry is enclosed in a wristwatch type case which also includes a constrictable band and an integral air bulb, resulting in an easily portable wrist-worn blood pressure measuring device. In another embodiment, the electronic circuitry is incorporated into a standard sphygmomanometer cuff to provide an automatic blood pressure measuring device.

10 Claims, 9 Drawing Figures

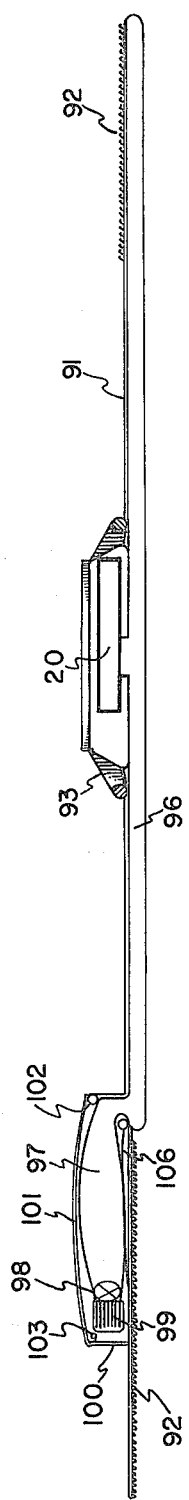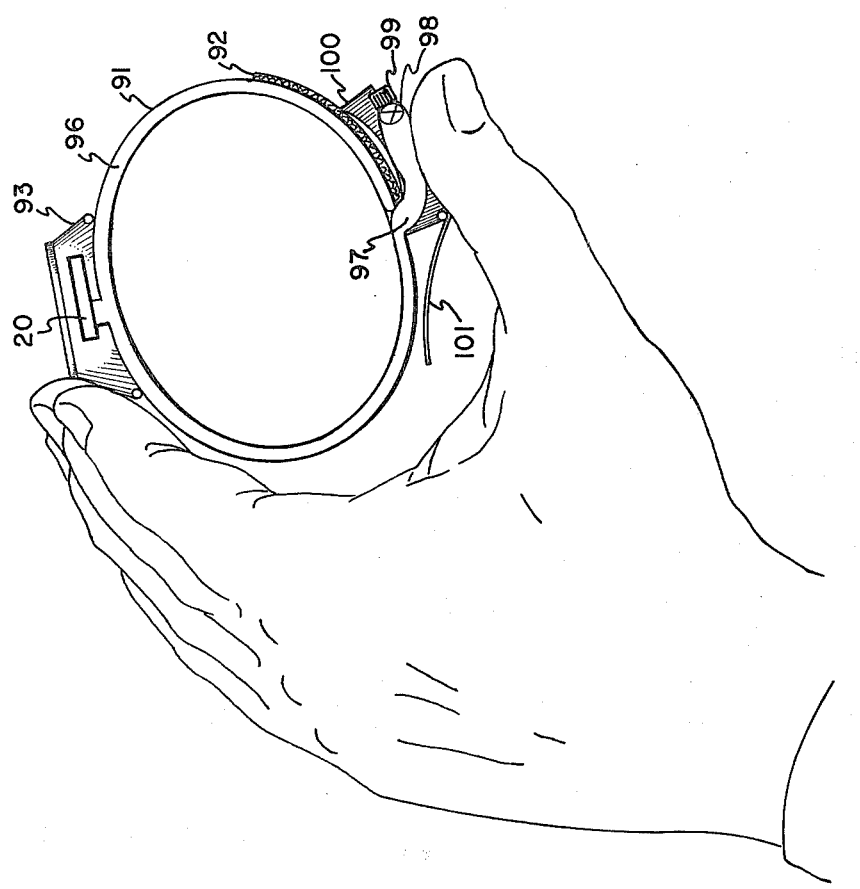

AUTOMATIC BLOOD PRESSURE MEASUREMENT DEVICE WITH THRESHOLD COMPENSATION CIRCUITRY AND METHOD FOR PERFORMING THE SAME

CROSS REFERENCE TO RELATED APPLICATION

The present application is a continuation-in-part application of U.S. patent application Ser. No. 9,377, filed Jan. 2, 1979, now abandoned.

TECHNICAL FIELD

The present invention relates to blood pressure measurement devices and in particular to devices which can automatically determine the systolic and diastolic pressures of an individual without the need for third party assistance.

BACKGROUND ART

This invention relates to blood pressure measurement devices, and particularly to blood pressure measurement devices that function automatically.

As is well known, the blood pressure of an individual varies during each ventricular heart beat from a high or systolic pressure to a rest or diastolic pressure. Such pressures are typically 120 millimeters of mercury (mm Hg) and 80 mm Hg for a healthy adult.

In the past, blood pressure measuring devices or sphygmomanometers were almost exclusively used by doctors and medical technicians (collectively called testing persons in this document) because of the difficulty in ascertaining accurate blood pressures of a patient. Such a standard sphygmomanometer consists of a pressurizing cuff which is placed over the patent's upper arm in juxtaposition to the patent's brachial artery. The cuff is then inflated by use of an air bulb while an analog dial gauge display, or a column of mercury, shows the pressure of the cuff. The cuff is inflated to completely occlude the flow of blood in the artery and the testing person listens with a stethoscope to ascertain this fact. By gradually lowering the pressure in the cuff, the testing person listens for the first sounds associated with arterial blood flow, known as the Korotkoff sounds. The cuff pressure at this point corresponds to the patient's systolic blood pressure.

By further reducing the cuff pressure, the testing person continues to hear surges of blood flowing through the artery during times when the blood pressure is greater than the cuff pressure, with occlusion of the arterial blood during the period of time that the blood pressure is lower than the cuff pressure. When the cuff pressure is reduced to a point where the surges are no longer heard (i.e., no arterial occlusion), the diastolic blood pressure reading is taken. Thereafter, the cuff is completely deflated, concluding the blood pressure measurement. In order to guarantee accurate results, the testing person must be well trained and familiar with the nature of the Korotkoff and other sounds typically heard through the stethoscope.

The last few years have seen a great increase in the public's awareness to the importance of careful monitoring of blood pressure in the avoidance of heart attacks and strokes. A great number of people have purchased sphygmomanometers for personal use without the requisite training and experience necessary to achieve accurate results. The present invention provides a compact, easily operated blood pressure measuring device which requires little skill or experience to operate and provides highly accurate results.

Although a number of prior art references disclose blood pressure monitoring devices which automatically determine systolic and diastolic pressures, none disclose or suggest the particular techniques utilized in the present invention including the use of a pressure transducer coupled to an analog amplifier which in turn is regulated by a sample and hold and logarithmic (log) converter for producing an output signal to accurately determine the occurrence of systolic and diastolic blood pressures. In particular, the present invention can be used with various individuals having much different blood pressure characteristics as well as body sizes while still providing accurate readings.

The present invention further provides control logic circuitry which automatically controls the sampling and holding of the received analog signal as well as controlling the operation of both a systolic and diastolic display. The present invention further uses the pulsating portion of the transducer blood pressure signal for determining which readings correspond to the systolic and diastolic pressures.

Although U.S. Pat. No. 4,078,551, Wohltjen et al discloses a sphygmomanometer having a pulse detector coupled to a pressure transducer to detect the superimposed electrical pulses for determining systolic and diastolic pressure measurements, it does not disclose or suggest the use of a sample and hold circuit in combination with a log compensation circuit under the control of control circuitry for providing a feedback control signal to the received pressure signal so as to be usable with various patients. Furthermore, Wohltjen et al does not disclose or suggest use of a dual display in which one of the dual displays constantly monitors the pressure within the pressurizing cuff used to make the physical measurements of the blood pressure.

Other prior art references such as U.S. Pat. No. 3,978,848, Yen et al, discloses a blood pressure measuring apparatus which utilizes two transducers, namely a blood transducer and a sound transducer, wherein the latter transducer is used to electrically "hear" the Korotkoff sound of inrushing blood at the time that full occlusion of an artery is first withdrawn, thus representing systolic pressure. This technique is of course different than that utilized in the present invention. This reference also neither discloses nor suggests the sample and hold and logarithmic feedback control system used in the measuring process of the present invention.

Another prior art reference; namely, an article in *Medical Electronics* by Looney, J. entitled "Blood Pressure By Oscillometry" (April, 1978, pp. 57–63), utilizes the pulsating or oscillometric pressure associated with a person's heartbeat to determine a maximum amplitude associated with minimum cuff baseline pressure so as to determine the mean arterial pressure. The oscillometric signal is not used to directly determine the time of the occurrence of systolic and diastolic pressures but is used to determine its maximum amplitude corresponding to mean arterial pressure and then extrapolating therefrom to calculate the systolic and diastolic pressures. The present invention clearly presents a determination of a systolic pressure occurrence when the fluctuating pulse pressure output exceeds the threshold detector so as to allow the analog to digital converter to measure a systolic pressure at the first occurrence of this output. The diastolic pressure occurs at the time that the threshold value is no longer maintained. It thus represents a departure from the disclosure in the Looney article.

U.S. Pat. No. 4,154,238, Link, discloses an apparatus and process which uses the second time derivative of the oscillometric waveform for determining the occurrences of systolic and diastolic pressures. According to the reference at column 2, lines 31–44, when the applied cuff pressure is approximately between the diastolic and systolic pressures of the blood vessel, there exists a negative spike in the second derivative. This negative spike essentially disappears when the applied cuff pressures correspond to diastolic and systolic pressures. Such time derivatives of the pulsatable effects generated by the blood vessels to determine the occurrence of systolic and diastolic pressure are not utilized in the present invention. This reference also neither discloses nor suggests the sample and hold and logarithmic compensating circuitry of the present invention.

Other references which were cited during the preparation and prosecution of the parent application are believed to be of lesser relevance, including U.S. Pat. Nos. 3,937,004, Natori et al; 4,063,551, Sweeney; and 3,391,691, Young.

In addition to the prior art cited, a commercial blood pressure measuring apparatus comprises a large bulky unit incorporating a chair, an automatic pressurizing cuff, and a large digital display screen. The drug store blood pressure measuring apparatus operates similar to the method traditionally used by doctors using ordinary sphygmomanometers and stethoscopes. A microphone is positioned in the pressurizing cuff and differences in sound output corresponding to total artery occlusion, partial occlusion and free blood movement is sensed by circuitry in the device to determine the systolic and diastolic pressure points. Additional components are necessary to determine the pressure of the cuff at these points so the microphone is used as a sensing device rather than as a measurement device.

This device is often located in well traveled areas of stores in order to attract prospective users. This can result in inaccurate blood pressure readings, as an individual is often excited and nervous about the presence of many other people around him or her. The present invention besides being easily carried by a person at all times, operates in a manner much different from these machines. The present invention directly utilizes the electrical output from the pressure transducer to determine the systolic and diastolic pressure.

OBJECTS OF THE INVENTION

It is therefore a principal object of the present invention to provide a blood pressure measurement apparatus which uses a single pressure transducer as a means for determining all appropriate blood pressure criteria.

It is another object of the present invention to provide an automatic blood pressure measuring device which requires no particular skill in order to operate it.

It is another object of the present invention to provide a blood pressure measurement apparatus having high accuracy.

It is yet another object of the present invention to provide a blood pressure measuring apparatus which in one embodiment is extremely compact and may be carried or worn by a user at all times.

A further object of the present invention is a blood pressure measurement apparatus that utilizes sample and hold and logarithmic circuitry for automatically scaling the received AC signal so as to properly determine the occurrence of systolic and diastolic pressures for a wide variety of patients.

Another object of the present invention is a blood pressure measurement apparatus of the above description which utilizes control circuitry to automatically initiate pressure measurements and control display of systolic and diastolic pressures.

A still further object of the present invention is a blood pressure measuring apparatus of the above description having two displays, one of which shows the current occluding cuff pressure until the diastolic pressure is determined, thereby indicating to the individual the current pressure in the cuff especially when initially pressurizing the cuff.

The invention accordingly comprises the features of construction, combination of elements, and arrangement of parts which will be exemplified in the construction hereinafter set forth, and the scope of the invention will be indicated in the claims.

DISCLOSURE OF THE INVENTION

The present invention is an easily operable, highly accurate, blood pressure measuring apparatus which comprises a pressure transducer coupled to a cuff that is pressurized by an air pump. The transducer is connected by electronic circuitry capable of translating the pressure transducer output into blood pressure readings. The device may be embodied into a case which may be worn like a wristwatch or into a standard sphygmomanometer cuff placed around the user's upper arm.

The circuitry senses the electrical output of the pressure transducer which is responsive to both the cuff pressure and the change in this cuff pressure due to arterial blood flow through the artery being measured. The output from the transducer comprises an electrical DC component which corresponds to the pressure applied to the cuff by the air pump. The output also comprises an AC or ripple component which corresponds to the pulse flow of blood through the artery.

When the flow of blood is totally occluded in the artery due to a high cuff pressure, only the DC component is present in the transducer output. The circuitry comprises an analog to digital converter that transforms the analog signal from the pressure transducer into a digital output. This output is presented to a first display which shows the cuff pressure at all times so that the user can apply a sufficiently high cuff pressure without going above some desired pressure It has been experimentally found that a totally occluded artery still generates a small half-wave rectified shaped voltage during each heart beat as a result of the elastic nature of the artery. Though this voltage is relatively small for some individuals, it can in others be greater than the threshold voltage used to determine the occurrence of the systolic pressure In order to avoid erroneous reading, a sample and hold module and a logarithmic converter module are used to sample, hold and scale all AC voltages amplified from the transducer. In this way, the noise pulses can be reduced and the spike-like pulses associated with the flow of blood through the artery can be differentiated.

Thus as the cuff pressure is reduced by release of air through a calibrated needle valve, arterial blood flow begins. The cuff pressure when blood flow first occurs is the systolic blood pressure. This flow of blood creates a small spike-like AC component in the transducer output which is sensed by a threshold module of the electronic circuitry.

The sample and hold module and the log converter module are under the control of a control module and are first enabled by a first control signal (control logic A), which is first enabled by activation of the control circuits. Once enabled, these modules suppress all arterial induced noise and thus delay the next output of the threshold module until the systolic AC component is detected.

Upon receipt of a systolic enable signal from the threshold module, the analog to digital converter is again enabled. This device converts the transducer output into a blood pressure reading and displays it on a second digital output reserved for displaying the systolic pressures. The control module controls the loading and displaying of the systolic pressure on this second display. The digital display is updated at the frequency of the patient's heart rate as the pressure of the cuff is further reduced. When the diastolic pressure point is reached, the AC component disappears and the analog to digital converter is no longer operative. The digital output at this point is then maintained at the first display to show the user's diastolic blood pressure. No further cuff pressures are shown on this first display since the blood pressure measurements are then complete.

It can be seen that the transducer output is thus utilized to determine the points at which the systolic and diastolic pressures are to be taken. It also gives the corresponding blood pressure at these points.

BRIEF DESCRIPTION OF THE DRAWINGS

For a fuller understanding of the nature and objects of the invention, reference should be had to the following detailed description taken in connection with the accompanying drawings, in which:

FIGS. 2A-2C are put together;

FIG. 3 is a cross-sectional side elevational view of one embodiment of the blood pressure measurement apparatus shown in FIG. 1, illustrating the physical construction of a wrist-worn case;

FIG. 3A is a cross-sectional side elevational view of the device embodiment of FIG. 3, shown in operation around a user's wrist;

BEST MODE FOR CARRYING OUT THE INVENTION

Figure 1:
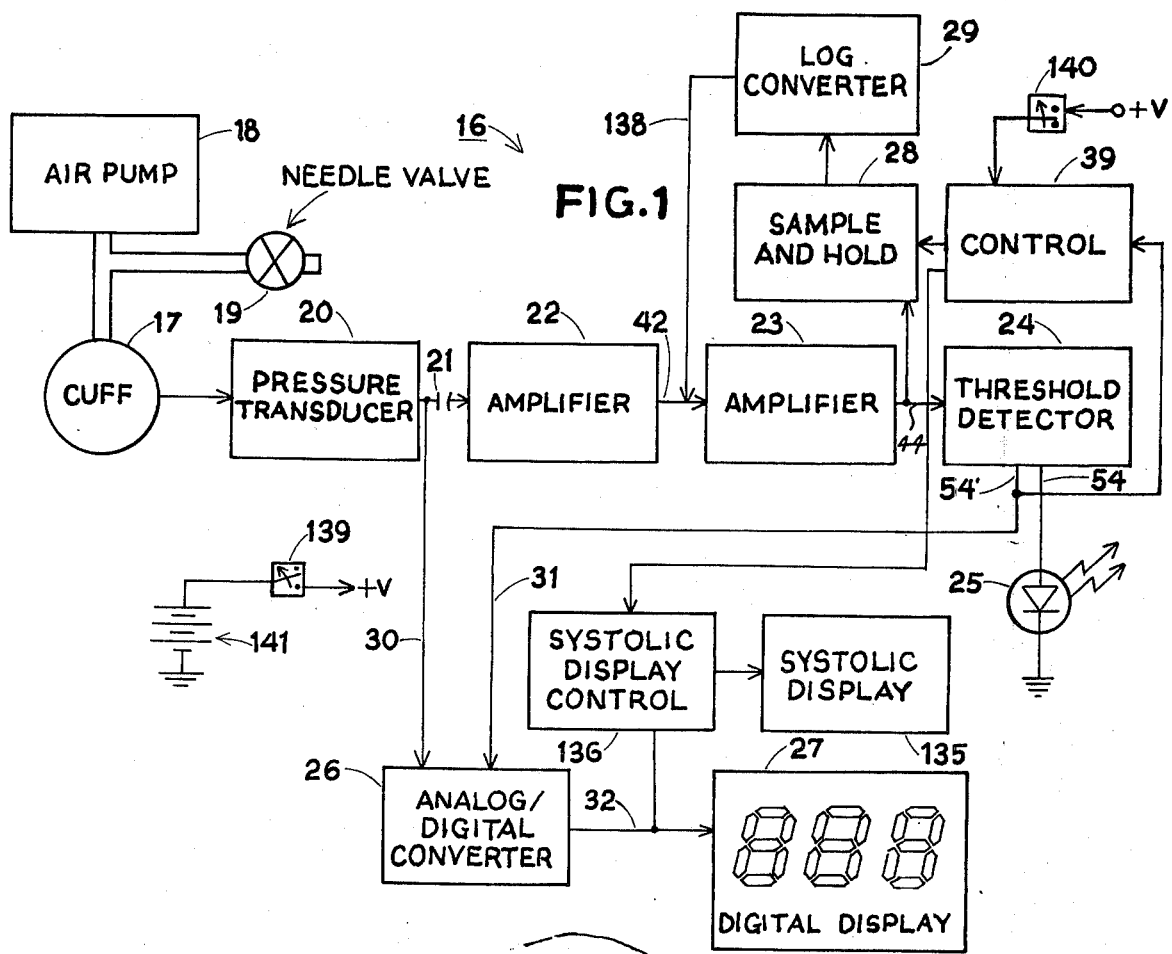
FIG. 1 is a block diagram of a blood pressure measurement apparatus of the present invention.

Referring to FIG. 1, there is shown a block diagram of a blood pressure measurement apparatus 16 comprising a pressure transducer 20, filter capacitor 21, amplifiers 22 and 23, a sample and hold module 28, a logarithmic converter module 29, control module 39, threshold detector 24, light emitting diode 25, analog to digital converter 26, a first digital display 27, a second (systolic) digital display 135, and a systolic display control module 136. The input of the pressure transducer 20 is responsive to the air pressure within a cuff 17 pressurized by an air pump 18. The output of the pressure transducer is an electrical signal which is fed both to the input 30 of the analog to digital converter 26 and to filter capacitor 21. The filter capacitor 21 removes any direct current (DC) component of the pressure transducer output. The filtered signal is amplified by amplifiers 22 and 23 and then applied to the input of threshold detector 24. One output 54' from threshold detector 24 is applied to the ENABLE or START CONVERT input 31 of the analog to digital converter and to the control module 39. Another output 54 from threshold detector 24 energizes the light emitting diode 25. The output of the analog to digital converter 32 is directly applied to the input of the first digital display 27. This display shows the current cuff pressure and decreases until the diastolic blood pressure point is reached. At this point the output on this display is held until the apparatus is turned off. This display thus shows the user the current pressure applied to the cuff and can be used as a safeguard to prevent over pressurization of the cuff as well as to indicate that the unit is operating properly while the air is being released by needle valve 19.

Figure 4:
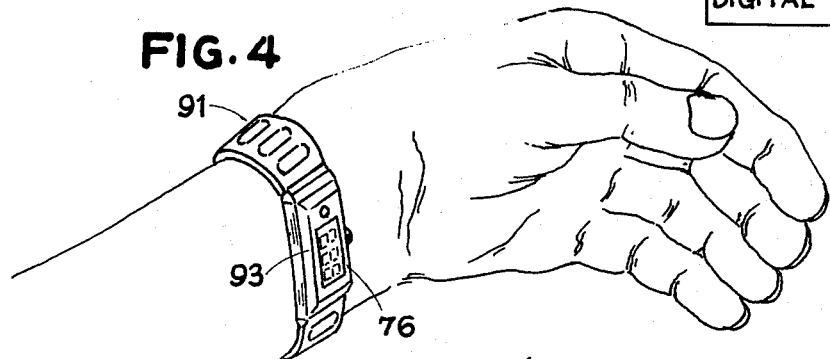
FIG. 4 is a perspective view of the embodiment of the blood pressure measurement apparatus shown in FIG. 3, shown in its operating position.
Figure 5:
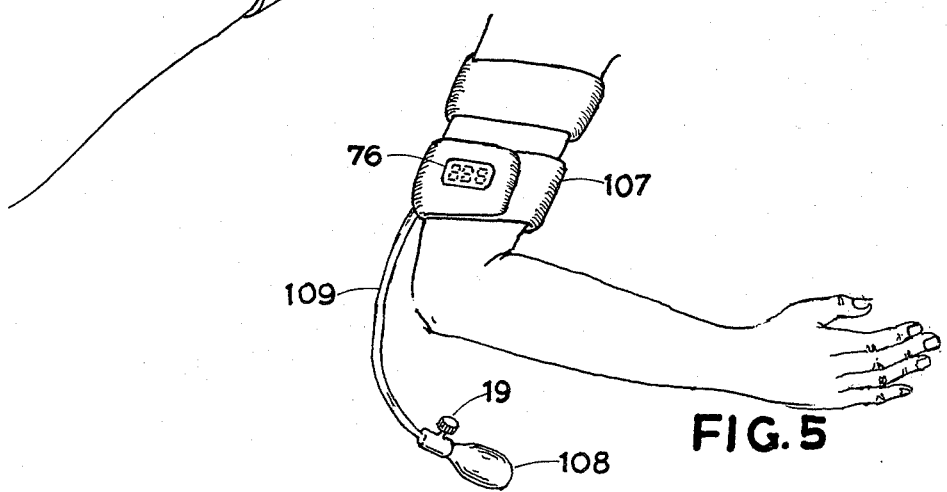
FIG. 5 is a perspective view of another embodiment of the blood pressure measurement apparatus shown in FIG. 1, illustrating its incorporation into a standard sphygmomanometer cuff.

When in operation, the pressure transducer 20 is coupled with a constrictable wristband embodying cuff 17 (see FIG. 4) or with a standard sphygmomanometer cuff positionable about the user's upper arm (see FIG. 5). The input to pressure transducer 20 therefore corresponds to the pressure of the cuff on the wrist or on the arm of the individual user. The cuff in either embodiment is designed to completely occlude the flow of blood through the user's artery at a point where the blood pressure is taken. The air pump 18 or other pressurizing means is capable of being slowly depressurized through a calibrated needle valve 19 to allow partially occluded blood flow through the artery and also to allow totally unrestricted blood flow through the measured artery. The needle valve in the preferred embodiment is manufactured by C.A. Norgren Company of Littleton, Colo. 80120 and is calibrated to release air from the cuff at a preferred rate of 3 mm Hg per second.

When the flow of blood is partially occluded through the user's artery, an additional pressure component corresponding to the pressure created by surges of blood as they pass the point of arterial compression is applied to the pressure transducer input. The output of pressure transducer 20 therefore is an electrical signal comprising a direct current (DC) voltage component corresponding to the constricting band or cuff pressure and a small, spike-like alternating current (AC) voltage component corresponding to the pressure created by the surges of blood. The frequency of the AC component is the patient's heart rate. Filter capacitor 21 removes the DC component from the pressure transducer output allowing only the AC component to be amplified by amplifiers 22 and 23.

Furthermore, there is another fluctuating voltage generated when the artery is totally occluded due to the elastic nature of the arteries. This voltage has a half-wave rectified shape and for some individuals has a large enough amplitude to trigger the threshold detector if amplifier 23 is not properly compensated.

It has been experimentally found that such factors as the user's body size, absolute blood pressure, and cardiac output tend to vary this occluded arterial voltage pulse. In order to insure that threshold detector 24 properly determines systolic and diastolic pressure points, a logarithmic compensation module 29 is utilized. This compensation module receives a sampled and held signal of output 44 through sample and hold module 28. The output 138 of the log compensation module is connected to the input 42 of amplifier 23 in a negative feedback relation. Thus the output 44 of amplifier 23 reduces the occluded arterial voltage pulse noise so that the threshold detection 24 can unambiguously determine the systolic and diastolic pressure points.

In order to sample the AC component at the proper times, a control module 39 is employed. This module is also used to control enablement of the systolic display control module 136.

Once the sample and hold module is first enabled by control module 39, the logarithmic compensation module will delay the next output from amplifier 23 until the output 44 is above the preset threshold voltage level of threshold detector 24. At this point, the threshold detector changes the status of its outputs 54 and 54' so as to energize light-emitting diode (LED) 25, to trigger the analog to digital converter 26, and to trigger the control module 39. The LED is used to further indicate to the user that the unit is operating properly. It need not be used in all embodiments of the present invention.

When the analog to digital converter 26 senses a pulse on the ENABLE line 31 from the threshold detector 24, the converter 26 converts the analog signal on input line 30 into the digital output on line 32. The digital signal on line 32 is interpreted by the first digital display 27 and the corresponding numerical value is thus displayed. This display is updated with each new digital pressure value that is generated on output line 32.

As best seen in FIG. 1, the output line 32 is also connected to the systolic display control module 136. This module receives the output from the analog to digital converter 26 and upon receipt of a proper control signal from the threshold detector, namely a control B pulse, enables the associated logic in the systolic display 135 and stores the value of the received signal from the analog to digital converter. Upon receipt of another control signal from the control module, namely control pulse C, the display driver of the systolic display 135 is enabled from the systolic display control module 136. At this point, the pressure which was received from the analog to digital converter 26 is shown in the systolic display 135. This display is maintained in the systolic display until the apparatus is turned off.

The first display 27 continues to show the analog to digital converter output as air is released from the cuff 17. At the point that no further AC components of the pressure transducer are detected, the threshold detector deactivates the analog to digital converter 26 so as to maintain the last received value in the first digital display. This particular value is equal to the diastolic pressure since the diastolic pressure is the pressure where the artery is not occluded during any part of the heart beat and thus represents the lowest pressure in the artery of the particular user.

In operation, the cuff 17 of blood pressure measuring apparatus is positioned about the patient's wrist or upper arm with the pressure transducer located adjacent to the patient's volar or brachial artery respectively. The switch 139 is then closed so as to power the electronic modules from battery 141. At this time the threshold detector generates pulses or outputs 54 and 54' to activate A/D converter 26 and LED 25 during each pump stroke since an AC component results from each stroke of air pump 18. The display thus shows the increasing pressure to cuff 17 allowing the user to stop the pumping operation at some desired point exceeding the user's systolic pressure. The display and LED also inform the user that the unit is operating properly.

Thus the air pump 18 or other cuff pressurizing means is activated to apply pressure through the cuff to the volar or brachial artery sufficient to completely occlude the artery and prohibit any flow of blood therethrough. It should be apparent that after the cuff has been so pressurized, the pressure transducer output comprises only a DC voltage component corresponding to the static pressure applied to the cuff and the occluded artery voltage pulses. The pressure transducer output is a voltage linearly related to the input pressure applied by the pressurizing means. The transducer output is applied to the input 30 of the analog to digital converter. During the time that the artery is totally occluded either the occluded arterial voltage pulses will trigger threshold detector 24 so as to redisplay the cuff occluding pressure or these pulses will be insufficient to trigger the threshold detector, whereby the last value into display 27 resulting from the pressurization or "pump up" process remains until the cuff pressure is controllably reduced.

After the cuff has been pressurized, the operation sequence is to energize the control circuitry by placing switch 140 in contact with the +V terminal. The control module 39 is then gated so as to generate a control pulse A which is used to activate the sample and hold module 28. At this point, a reading is taken from the output of amplifier 23 and compensated by the logarithmic compensator module 29 and applied back to the input of amplifier 23 so as to regulate its output 44 to the threshold detector 52. The output is logarithmically reduced so as to prevent occluded arterial pulses from exceeding the threshold voltage level of detector 24. Thus the compensation module 29 causes a delay in the next output of the threshold detector such that the next output corresponds to the systolic pressure point; that is, the pressure point when blood flow first occurs during a short period of each user heartbeat.

As the pressure in cuff 17 is slowly reduced by means of needle valve 19, a point is reached where the pressure of the blood at the point of constriction is greater than that generated by the cuff. Blood flow then occurs during a small portion of each heart beat. Blood passes the point of constriction in pressure surges at the heart rate of the user. These pressure surges are sensed by the pressure transducer 20 and their presence is indicated by a small alternating current output from the pressure transducer at the frequency of the user's heartrate. The point at which the maximum blood pressure equals that generated by the pressurizing means is the systolic blood pressure of the user.

The composite DC and AC output signal from the pressure transducer 20 is filtered by capacitor 21 to remove the DC component. The small AC components due to either occluded arterial pulses or partially occluded arterial blood flow are amplified by amplifiers 22 and 23 and applied to the input of the threshold detector 24 after logarithmic compensation by compensation module 29. This compensation insures that the occluded arterial pulses are sufficiently reduced so as not to exceed the threshold level of detector 24. The threshold level of detector 24 and the gain of amplifiers 22 and 23 as controlled by converter 39 is set so that the partially occluded AC component in the output of the transducer 20 exceeds the threshold value necessary to turn the threshold detector 24 ON. When this happens, the output from the threshold detector 24 serves a two-fold purpose. One output 54 is sufficient to light LED 25 which informs the user that the systolic pressure point has been reached. A second output 54' is applied to ENABLE line 31 of the analog to digital converter 26.

An input signal on the ENABLE line 31 acts as a "start convert" command which causes the analog to digital converter 26 to convert the analog signal present on input line 30 into a digitized electrical output signal on output line 32. The signal present on input line 30 comprises both DC and AC voltage components of the pressure transducer 20 output, but because all the AC components are small compared to the DC component, the value is essentially that of the DC component, corresponding to the pressure applied by the pressurizing means. This value in digital form is applied to the input of the digital display 27 and to the systolic display control logic module 136. There, upon receipt of the proper control signals, the systolic display is presented with the digitized value of the systolic pressure. This reading is maintained by the systolic display until switch 139 is opened.

As the cuff pressure continues to decrease, the pressure transducer output continues to comprise both DC and AC voltage components. The threshold detector 24 continues to deliver a signal to the ENABLE line 31 of the analog to digital converter each time the amplified AC component exceeds the preset threshold level. The output from the threshold detector is thus a series of pulses occurring at the heart rate of the user. Therefore the digital display 27 reflects the cuff pressure at all times. While the cuff pressure is slowly reduced, a point is reached where the minimum pressure in the artery is equal to that of the cuff. This is the pressure at which there is no occlusion of the artery by the cuff. When this occurs, there is no longer an AC voltage component in the pressure transducer output and the analog to digital converter 26 becomes inoperative. The number displayed on the digital display 27 then remains constant. This number corresponds to the diastolic blood pressure of the user corresponding to the steady state minimum pressure of the user's blood flow.

Figure 2A:
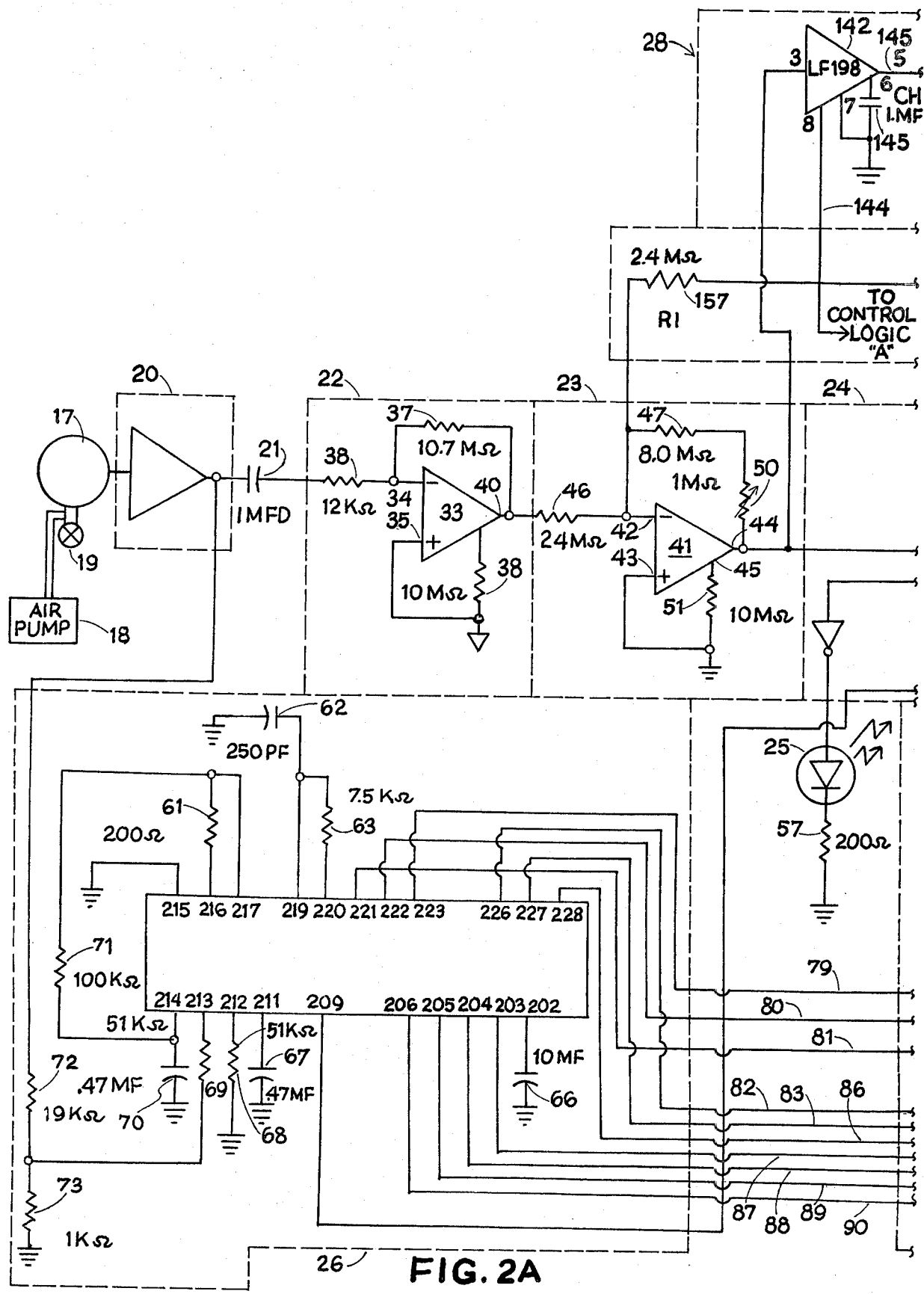
FIGS. 2A-2C form a schematic diagram of the blood pressure measurement apparatus shown in FIG. 1.
Figure 2B:
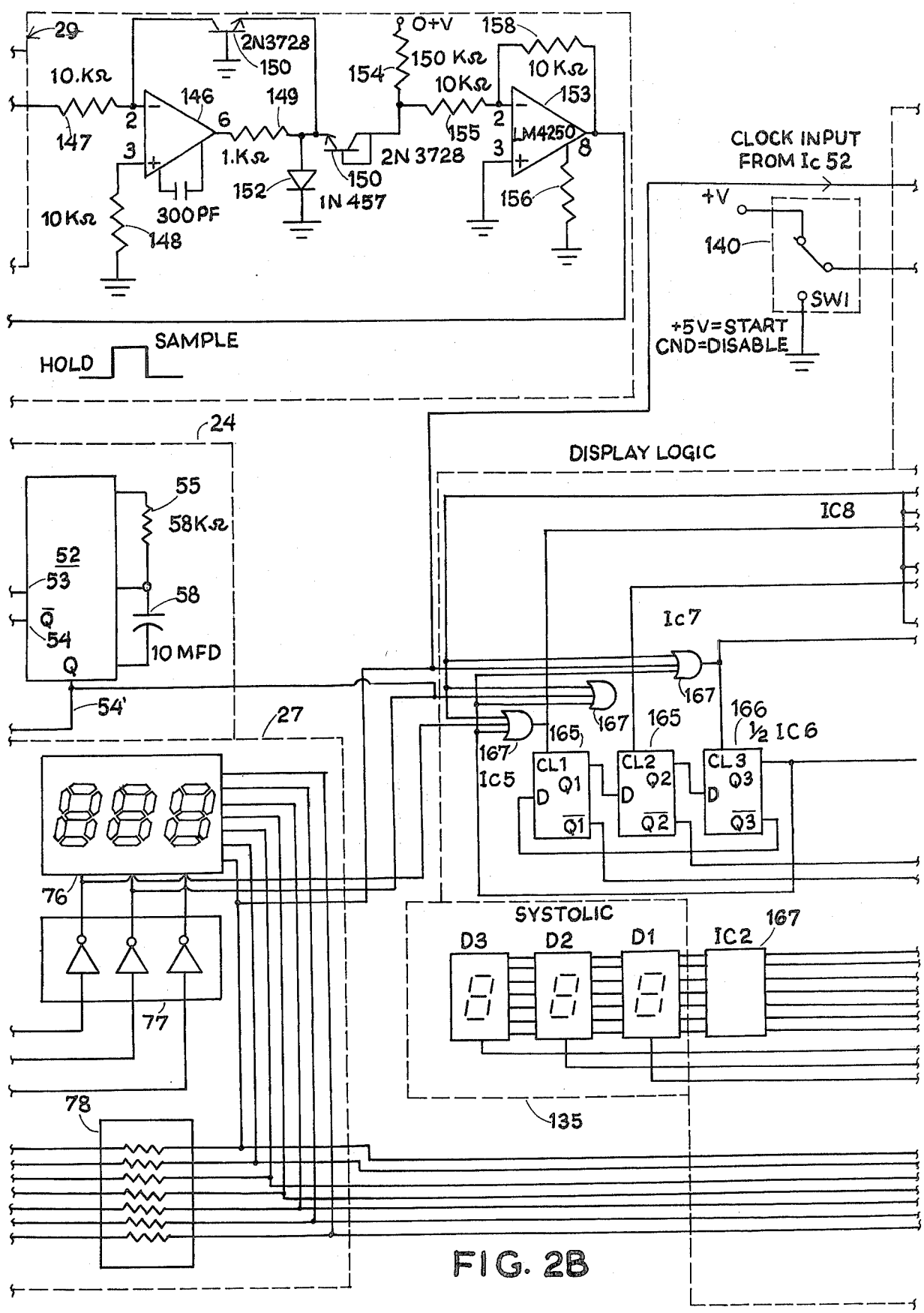
Figures 2C, 2D:
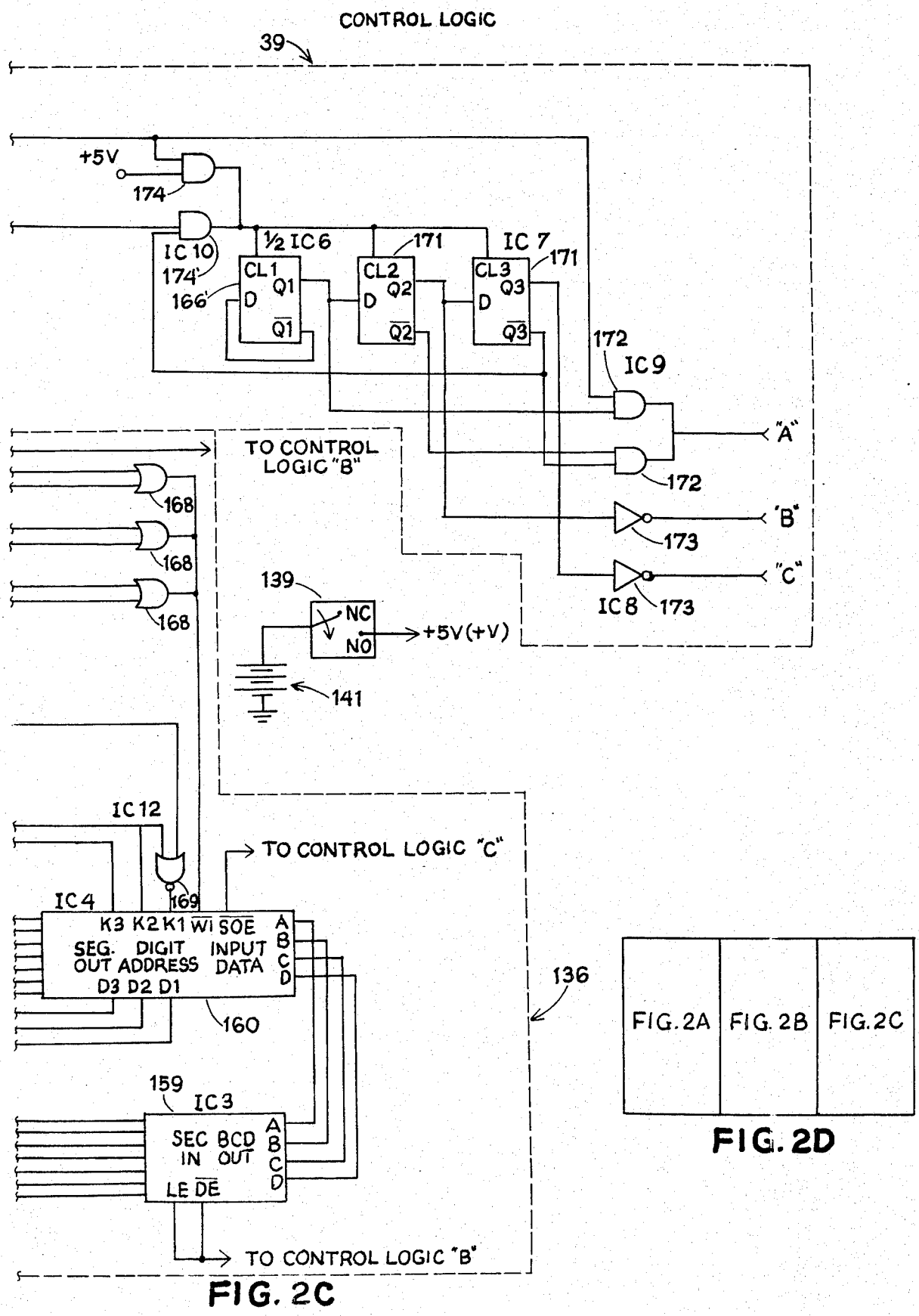
FIG. 2D is a diagram to show how

Referring now to FIGS. 2A-2C, there is shown a schematic diagram illustrating the electrical and electronic components which make up the blood pressure measurement apparatus shown in FIG. 1. The pressure transducer 20 is manufactured by National Semiconductor Corp. and has part number LX1701G. It consists of a piezoelectric strain sensor whose output is monitored by operational amplifiers located within the device. The sensor is coupled to the cuff. The transducer is calibrated during manufacture so that a zero input corresponding to complete depressurization of the pressurizing means results in an output of zero volts. The output voltage change of the pressure transducer is linear with respect to the input pressure. When the pressure applied by the pressurizing means is 300 millimeters of mercury (mm Hg), the output of the pressure transducer is 6 volts DC.

The filter capacitor 21 has a value of 0.1 microfarads. Amplifier 22 comprises operational amplifier 33 having negative and positive inputs 34 and 35, input resistor 36, feedback register 37 and power drain resistor 38. The input resistor 36 is connected between the filtering capacitor 21 and the negative input 34 of the operational amplifier 33. The feedback resistor 37 is connected between the output 40 of the operational amplifier 33 and the negative input 34. The drain resistor 38 is connected between the operational amplifier 33 and ground. Positive input 35 of the operational amplifier 33 is also connected to ground. Operational amplifier 33 is programmable by the drain resistor 38 to set its quiescent power drain at 1.8 microwatts.

The output of the operational amplifier 33 is a linear function with respect to the input with a small signal gain approximately equal to a ratio determined by the value of the feedback resistor over the value of the input resistor. Operational amplifier 33 is also manufactured by National Semiconductor Corp. having a part number LM4250. Input resistor 36 has a value of 12 kilohms, feedback resistor 37 has a value of 10.7 megohms and the drain resistor 38 has a value of 10 megohms.

Amplifier 23 comprises operational amplifier 41 having a negative input 42, a positive input 43, an output 44 and a drain 45. Amplifier 23 further comprises input resistor 46, feedback resistors 47 and 50 and drain resistor 51. Input resistor 46 is connected between output 40 of operational amplifier 33 and input 42 of operational amplifier 41. Feedback resistors 47 and 50 are connected in series between output 44 of operational amplifier 41 and negative input 42. Drain resistor 51 is connected between drain 45 and ground. Positive input 43 of the operational amplifier 41 is also connected to ground. Operational amplifier 41 is identical to operational amplifier 33. The input resistor has a value of 2.4 megohms, feedback resistor 47 has a value of 8.0 megohms, feedback resistor 50 is a variable resistor having a maximum resistance of 1 megohm and drain resistor 51 has a value of 10 megohms. The drain resistor 51 is chosen so that the quiescent power drain of operational amplifier 41 is also 1.8 microwatts. The feedback resistor 50 is used during calibration of the blood pressure measuring apparatus in order to set the gain of the operational amplifier 41.

The output 44 of amplifier 23 is also connected to a sample and hold circuit 28 which comprises an operational amplifier 142 and a capacitor 143. An input line 144 is connected to the A output of the control module 39 so that when activated, the signal on output 44 is sampled and held.

The output 145 of the sample and hold circuit is transferred to the input of the logarithmic converter 29. The logarithmic converter also includes an operational amplifier 146, resistors 147, 148 and 149, matched transistors 150 and 151, reverse protection diode 152, and an inverter/ buffer stage comprising operational amplifier 153 and resistors 154, 155, 156, 157 and 158.

Thus when a control logic signal A is received on input line 144, operational amplifier 142 samples the output of amplifier 23 and holds this value at its output (pin 6). This output is connected to the logarithmic converter by a resistor 147. The converter logarithmically limits the gain of this received signal through use of the matched transistors 150 and 151. Diode 152 prevents a reverse voltage from damaging these matched transistors. Operational amplifier 153 inverts and buffers this signal in combination with its associated resistors so that its output when presented through resistor 157 to the input 42 of amplifier 23 limits the amplifier's gain.

Table 1 is an illustration of the corresponding output values of the logarithmic converter depending upon the input from amplifier 23 for various voltages. The first column gives the voltage on input 42. The second column lists the corresponding voltage on output 44 of amplifier 23 when the sample and hold circuit and log converter circuit is inoperative. The third column lists the output voltage of buffer 153, pin 6, when the sample and hold circuit and log converter circuit is operating. The fourth column lists the voltage at input 42 of amplifier 23 when the sample and hold circuit and log coverter circuit is operating. This voltage is thus the algebraic difference between the output voltage given in column 1 and the log output voltage given in column 3. Finally, the fifth column lists the voltage at output 44 as compensated by the above circuits.

It is apparent from Table 1 that the output 44 of amplifier 23 is logarithmically reduced as its uncompensated value increases.

Since the threshold detector trigger voltage is preferably set at +1.55 volts, uncompensated inputs to amplifier 23 could trigger the detector for an AC pulse as low as 0.673 volts. For some individuals with strong heart beats, such a pulse can occur during totally occluded blood flow. This would result in an erroneously high systolic pressure reading. With the log compensation circuitry, an occluded arterial pulse greater than 0.961 volts will not trigger the detector. It has been experimentally found that such a value is not obtained for such occluded pulses and therefore false triggering of the detector is eliminated.

The values for the various components comprising the sample and hold module and logarithmic converter are presented in Table 2. Threshold detector 24 comprises monostable multivibrator 52 having an input 53 and an output 54. Threshold detector 24 further comprises resistor 55 and capacitor 56. The output 44 of operational amplifier 41 is connected to the input 53 which is the Schmitt trigger input of monostable multivibrator 52. The threshold level of the monostable multivibrator 52 is internally set during manufacture at +1.55 volts. During calibration of the blood pressure measuring apparatus, feedback resistor 50 is adjusted so that an AC partially occluded component in the transducer output exceeds the threshold level of monostable multivibrator 52. This pulse typically generates a peak pulse output of 1.75 volts with an activated log compensation circuit.

TABLE 1

| INPUT 42 (uncompensated) (volts) | OUTPUT 44 (uncompensated) (volts) | LOG OUTPUT (buffer 153) (volts) | INPUT 42 Minus LOG OUTPUT (compensated) (volts) | Compensated OUTPUT 44 (volts) |
|---|---|---|---|---|
| 0.384 | 1.00 | 0.000 | 0.384 | 1.00 |
| 0.480 | 1.25 | 0.096 | 0.383 | 0.998 |
| 0.576 | 1.50 | 0.176 | 0.400 | 1.042 |
| 0.673 | 1.75 | 0.243 | 0.430 | 1.118 |
| 0.769 | 2.00 | 0.301 | 0.468 | 1.217 |
| 0.865 | 2.25 | 0.352 | 0.513 | 1.334 |
| 0.961 | 2.50 | 0.397 | 0.563 | 1.465 |
| 1.057 | 2.75 | 0.439 | 0.618 | 1.607 |
| 1.153 | 3.00 | 0.477 | 0.676 | 1.759 |
| 1.250 | 3.25 | 0.511 | 0.738 | 1.919 |
| 1.346 | 3.50 | 0.544 | 0.802 | 2.085 |
| 1.442 | 3.75 | 0.574 | 0.868 | 2.257 |
| 1.538 | 4.00 | 0.602 | 0.936 | 2.434 |
| 1.634 | 4.25 | 0.628 | 1.006 | 2.616 |
| 1.730 | 4.50 | 0.653 | 1.077 | 2.801 |
| 1.826 | 4.75 | 0.676 | 1.150 | 2.990 |
| 1.923 | 5.00 | 0.699 | 1.224 | 3.182 |
| 2.019 | 5.25 | 0.720 | 1.299 | 3.377 |
| 2.115 | 5.50 | 0.740 | 1.374 | 3.574 |
| 2.211 | 5.75 | 0.759 | 1.451 | 3.774 |
| 2.307 | 6.00 | 0.778 | 1.529 | 3.976 |

TABLE 2

| Reference No. | Description (value) | | Comment |
|---|---|---|---|
| | Sample and Hold Module | | |
| 142 | sample and hold (I.C.) | | National Semiconductor (N.S.) #LF198 |
| 143 | Capacitor 1 uf | | |
| | Log Converter, Inverter/Buffer Module | | |
| 146 | Operational amplifier | | N.S. #LM101 |
| 147 | resistor | 10.0k | |
| 148 | resistor | 10.0k | |
| 149 | resistor | 1.0k | |
| 150 | Matched transistors | 2N 3728 | |
| 152 | diode | 1N 457 | |
| 153 | operational amplifier | | N.S. #LM4250 |
| 154 | resistor | 150k | |
| 155 | resistor | 10k | |
| 156 | resistor | 10M | |
| 157 | resistor | 2.4M | |
| 158 | resistor | 10.0k | |

When a signal greater than the threshold value is present at input 53, the output from monostable multivibrator 52 is a squarewave with a wave duration determined by resistor 55 and capacitor 56. Resistor 55 and capacitor 56 are electrically connected to the monostable multivibrator 52 according to instructions given in the manufacturer's literature. Monostable multivibrator 52 is manufactured by National Semiconductor Corp. having part number DM74121. Resistor 55 has a value of 58 kilohms and capacitor 56 has a value of 10 microfarads.

Analog to digital converter 26 is a monolithic digital voltmeter integrated circuit 60 manufactured by National Semiconductor Corp., having part number MM74C935. It has connecting pins 202, 203, 204, 205, 206, 209, 211, 212, 213, 214, 215, 216, 217, 219, 220, 221, 222, 223, 226, 227, and 228. These connecting pin numerals reflect the manufacturer's pin number designation by the addition of 200 to the manufacturer's pin number. Hence, number 202 refers to manufacturer's pin number 2, 215 refers to pin number 15, etc. The remaining connecting pins of the integrated circuit 60 are not shown in FIG. 2A as they do not bear directly upon the invention's operation. The necessary connections which must be made to these connecting pins are illustrated in the manufacturer's literature.

Analog to digital converter 26 also comprises resistor 61, capacitor 62, resistor 63, capacitor 66, capacitor 67, resistor 68, resistor 69, capacitor 70, resistor 71, resistor 72, and resistor 73. Resistor 61, having a value of 200 ohms, is connected between connecting pins 216 and 217 of integrated circuit 60. Capacitor 62, having a value of 250 picofarads, is connected between connecting pin 219 and ground. Resistor 63 has a value of 7.5 kilohms and is connected between connecting pins 219 and 220. Capacitor 66 is connected between connecting pin 202 and ground and has a value of 10 microfarads. Capacitor 67, having a value of 0.47 microfarads, is connected between connecting pin 211 and ground. Resistor 68, having a value of 51 kilohms, is connected between connecting pin 212 and ground. Capacitor 70, having a value of 0.47 microfarads, is connected between connecting pin 214 and ground. Resistor 71, having a value of 100 kilohms, is connected between connecting pin 217 and connecting pin 214. Connecting pin 215 is connected to ground. Resistor 72, having a value of 19 kilohms, has one end connected to connecting pin 217. The other end of resistor 72 is connected in parallel to resistor 73 and one end of resistor 69. Resistor 69, having a value of 51 kilohms, has its other end connected to connecting pin 213. The other end of resistor 73, having a value of 1 kilohm, is connected to ground.

Output 54' of the monostable multivibrator 52 is connected to connecting pin 209 of integrated circuit 60 while output 54 is connected to the anode of the light emitting diode 25. The cathode of the light emitting diode 25 is connected to one end of resistor 57, having a value of 200 ohms. The other end of the resistor is connected to ground.

The digital display 27 comprises a three-digit, seven segment multiplexed light emitting diode display 76 a digital buffer 77 and segment resistors indicated generally as 78. Digital display 27 also includes digit input lines 79, 80, and 81 and segment input lines 82, 83, 86, 87, 88, 89, and 90. Digit input lines 79, 80, and 81 are connected to the inputs of digital buffer 77. Digit input line 79 is also connected to connection pin 223 of integrated circuit 60. Digital input line 80 is connected to connecting pin 222 of integrated circuit 60 and digital input line 81 is connected to connecting pin 221 of integrated circuit 60. Segment input lines 82, 83, 86, 87, 88, 89, and 90 are all connected to the inputs of segment resistors 78. The output from each of the segment resistors 78 is connected to the segment input of the LED display 76. Segment line 82 is also connected to connecting pin 226 of integrated circuit 60. Segment line 83 is connected to connecting pin 227, segment line 86 is connected to connecting pin 228, segment line 87 is connected to connecting pin 203, segment line 88 is connected to connecting pin 204, segment line 89 is connected to connecting pin 205 and segment line 90 is connected to connecting pin 206. Lines 79, 80, 81, 82, 83, 86, 87, 88, 89, and 90 carry information from the analog to digital converter 26 in a form that can be interpreted by the digital display 27 in order that LED display 76 displays the blood pressure data received from pressure transducer 20. The LED display 76 displays blood pressure in units of millimeters of mercury (mm Hg).

Thus digital display 27 shows the user's blood pressure firstly when switch 139 is closed and cuff 17 is pressurized which allows the user to know that the unit is operating properly and also shows the user when a pressure has been obtained which will totally occlude arterial blood flow. Then upon closing of switch 140, the control circuitry 39 (see FIG. 9) is energized so that the sample and hold circuit 28 and the logarithmic converter module 29 are activated. The subsequent readings taken by the analog to digital converter 26 firstly represent the systolic pressure and subsequently represent the pressure within the cuff as the needle valve deflates the cuff until a point is reached in which the threshold detector ceases to produce output pulses on output lines 54 and 54'. This in turn "freezes" the last number on display 27. This last number, as previously indicated, is the diastolic blood pressure number. Display 27 therefore hows a full range of blood pressure readings down to the diastolic pressure at which point its reading is fixed until the unit is deenergized.

In addition to segment input lines 82, 83 and 86–90 being connected to display 27 through segment resistor 78, a connection is also made to the systolic display control module 137 as best seen in FIGS. 2 and 2B–2C.

The systolic display control module comprises a segment to binary coded decimal output converter 159 which converts the segment output line information into a BCD number on its output lines A, B, C, and D. The output of this segment converter is interconnected to a display controller/driver 160 when the BCD converter sees a control logic "B" signal from the control module 39. The display controller/driver converts the input data into a seven segment information format and stores it in its memory when a $\overline{\text{WRITE ENABLE}}$ ($\overline{\text{WE}}$) signal enters its low voltage state which in turn is controlled by the control logic "B" input pulse from the control module 39. Display controller/driver 160 is addressed through the decoded outputs of dual flip-flop 165 and one half of dual flip-flop 166. These flip-flops take digital information from the inverted outputs of A-D converter 60 such that when a control pulse "B" signal is low from the control module 39, data for the systolic display 135 is stored in the memory portion of display controller/driver 160. The control input "C" signal entering the low voltage state is used to trigger the $\overline{\text{SOE}}$ input of display controller/driver 160 so as to latch the information onto digits D1, D2 and D3 of the driver until power to the circuit is turned off. The outputs D1, D2 and D3 of driver 160 are interconnected with systolic display 135 and in combination with resistor network 167 presents the segment out information to the systolic display three digit numerals in a manner analogous to that for display 27. Gates 167, 168 and 169 are used to gate information into the display controller/driver 160.

Finally, the control module 39 comprises switch 140, one-half of dual flip-flop 166 (designated by the numeral 166'), a second pair of dual flip-flops 171, dual AND gates 172, inverters 173 and dual AND gates 174. In operation, clock pulses from output 54' of threshold detector integrated circuit 52 are gated by AND gate 174 when switch 140 contacts the plus V input energized by battery 141. Flip-flop 166' and dual flip-flops 171 count and decode the incoming pulses. Since switch 140 is not put into the +V position until after the cuff has been fully pressurized, the first output pulse from AND gates 172 (to control output "A") is used to enable the sample and hold module 28. After the sample and hold module is activated, the logarithmic compensation circuit 39 (see FIGS. 2A–2B) negatively feeds its signal back to the second amplifier 23 so as to prevent threshold detector integrated circuit 52 from generating another output on output line 54' until the threshold value is obtained corresponding to the point at which the first rush of blood through the artery occurs (corresponding to the systolic blood pressure). This next pulse causes the generation of the "B" pulse from the control module 39 which enables the BCD converter 159, causing the value to be stored in the display controller/driver 160. The next output from line 54' causes the generation of the control pulse "C" output from control module 39 which in turn enables the display driver input $\overline{\text{SOE}}$ of display controller 160 so as to energize the normally OFF display 135. Thus, the systolic display is latched on and indicates the systolic pressure reading. This value is maintained since the display controller/driver 160 does not receive any further pulses from control module 39 after the generation of the control "B" and control "C" pulses.

Details of the components used in the systolic display control module 136 and the control module 39 are set forth in Table 3.

Thus it is readily apparent that the systolic display 135 is controlled so as to only show the systolic display while display 27 shows all of the blood pressure readings taken when the unit is energized and remains at the diastolic blood pressure once that reading is made.

The part numbers and manufacturer of the component of the blood pressure measurement device previously described are given only as illustration. One skilled in the art would be able to replace those components with one of equivalent function.

TABLE 3

| Ref. No. | Description (value) | Comment |
| --- | --- | --- |
| | Systolic Display Control Module | |
| 159 | Seven segment to BCD converter/latch | N.S. #MM54C915 |
| 160 | Display controller/driver | N.S. #MM74C917 |
| 165 | Dual D flip-flops | N.S. #MM74C74 |
| 166 | Dual D flip-flops | N.S. #MM74C74 |
| 167 | Three input OR gates | N.S. #CD4075 |
| 168 | Two input OR gates | N.S. #MM54C32 |
| 169 | NOR gate | N.S. #54C02 |
| | Control Module | |
| 140 | Single pole double throw switch | |
| 166' | See 166 above | |
| 171 | See 166 above | |
| 172 | AND gates | N.S. #MM54C08 |
| 173 | Inverters | N.S. #MM54C04 |
| 174 | AND gates | N.S. #MM54C08 |

Referring now to FIG. 3, there is shown a side elevational cross-sectional view of the blood pressure measurement apparatus embodied as a wrist-worn device. The device comprises an elongated cloth band or strip 91 incorporating hook and loop fasteners at the other end. These hook and loop fasteners, commonly sold under the Velcro trademark, allow the cloth band to be securely tightened about the wearer's wrist. The Velcro strips are designated as numeral 92. The device further comprises a housing 93 which encloses the sensing and display circuitry and the pressure transducer 20. A thin elongated inflatable air bladder 96 is mounted to the underside of the cloth bank 91 so that it is in contact with the wearer's skin when the cloth band 91 is tightened about the wearer's wrist. One end of the inflatable air bladder 96 defines an air bulb 97 having a check or valve 98 which is controlled by rotating the knurled nob 99. The air bladder corresponds to cuff 17 and the air bulb corresponds to air pump 18 shown in FIGS. 1 and 2A. A needle valve 19 may be used instead of check valve 98. The air bulb 97 and check valve 98 are enclosed within housing 100 which incorporates a cover 101 attached to housing 100 at one end by a hinge 102 and at its other end by a latch 103. An arched leaf spring of spring steel 106 is mounted to the bottom of the housing 100 and is forced into a flattened flexed position by air bulb 97 whenever the cover 101 is closed.

In order to operate the device, the wearer positions the housing 93 enclosing the pressure transducer 20 over the volar artery in his wrist. The housing 93 is held in this position by securely tightening the cloth band about the wearer's wrist by use of the Velcro strips 92. FIG. 3A illustrates the device in position about the wearer's wrist. Once the housing 93 and transducer 20 are securely in position, the cover 101 of the housing 100 is opened, exposing air bulb 97. The spring steel strip 106 then is free to return to its arched position. In its relaxed position, the steel strip 106 forces the air bulb 97 up slightly and into its operating position. The check valve 98 is closed by rotating the knurled knob 99 to its closed position, permitting only intake air to enter the air bladder therethrough. The air bulb 97 is then compressed repeatedly in order to inflate the air bladder 96 and occlude the blood flow through the volar artery of the wearer's wrist. FIG. 3A illustrates one possible method that may be used to compress the air bulb 97. When blood flow through the volar artery has been occluded, the check valve 98 is opened slightly by rotating the knurled knob 99 slightly.

As the pressure from the air bladder 96 slowly escapes, the user carefully observes the digital displays 135 and 27 located within the housing 93 to determine his or her systolic and diastolic blood pressure, as described above. As the pressure is slowly reduced, display 27 flashes at the user's heartrate, continually updating the display with the air bladder pressure. When the display ceases to flash and remains constant, the diastolic pressure point is reached and pressure displayed on display 27 is the diastolic pressure. When the diastolic blood pressure has been determined, the check valve 98 may be opened completely, allowing all the air to escape from the air bladder 96. Switches 139 and 140 are then opened to de-energize the unit. The device may be then removed, repositioned, or left in its measuring position indefinitely to be available whenever the wearer desires an additional blood pressure reading to be taken.

FIG. 4 is a perspective view showing the device in its measuring position adjacent to the volar artery of the wearer's wrist.

FIG. 5 illustrates an alternate embodiment where the blood pressure measuring apparatus is incorporated into a standard sphygmomanometer cuff 107 having a remote air bulb 108 and connecting hose 109. This embodiment is not as portable as that worn on the wrist but does automatically give the systolic and diastolic blood pressure of the wearer without the use of a stethoscope or additional instruments.

The blood pressure measurement apparatus previously described is adaptable to various pressurizing means, such as a wrist-worn case or a sphygmomanometer cuff. A single pressure transducer is responsive to both the externally applied pressure and to the presence of blood flow in the artery. By sensing the degree of artery occlusion caused by the external pressure, the systolic and diastolic blood pressure of the wearer can be determined. Sample and hold, logarithmic compensation, and control circuit insure that the proper systolic and diastolic pressure points are measured regardless of the physical characteristics of the user. No special skill or additional components are necessary for its use.

When adapted to a wrist-worn case, it is possible that the case can contain an electronic watch circuit, so that the utility of the device is greatly increased.

It will thus be seen that the objects set forth above, among those made apparent from the preceding description, are efficiently attained and, since certain changes may be made in the above construction without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Having described the invention, what is claimed is:

1. A blood pressure measurement device comprising:
(A) an inflatable cuff positionable about a user's limb and pressurizable so as to temporarily stop the flow of blood of the artery constricted by the cuff;
(B) means for pressurizing the cuff so as to produce a pressure within the cuff to totally occlude blood flow through the artery;
(C) means, activatable for gradually deflating the pressurized cuff to a pressure less than the diastolic pressure of the artery;
(D) a transducer coupled to the cuff and positioned to be placed in juxtaposition to the artery and having an electrical output simultaneously responsive to the pressure applied by the pressurizing means to the cuff and to the fluctuating pulse pressure components in the cuff pressure due to occluded arterial pressure pulses or to the presence of blood flowing through the artery in a partially occluded manner;
(E) means connected to the transducer electrical output for only passing the fluctuating pulse pressure components of the electrical output;
(F) means connected to the fluctuating pulse pressure components output means, for electrically amplifying the fluctuating pulse pressure components;
(G) means, coupled to the output of the amplifying means, operative by a first control pulse, for sampling and holding the electrical output from the amplifying means upon receipt of the first electrical pulse;
(H) a compensation circuit, connected to the output of the sample and hold means for modifying the electrical output of the sample and hold means so as to diminish the amplitude of the output as a function of the output signal, the output of the compensation circuit connected to the amplifying means so as to effectively reduce the output of the amplifying means as a function of the compensation circuit output;
(I) a threshold detector, connected to the amplifying means output for enabling the output of the detector during initial inflation of the cuff when the sample and hold means is inoperative and when the amplified fluctuating pulse pressure components as modified by the compensation means is greater than a predetermined value representing when blood flow begins after arterial occlusion and continuing until arterial blood flow is completely unoccluded;
(J) an analog to digital (A-D) converter receiving as one input the output of the transducer and as a second input the output of a threshold detector, the A-D converter generating digital output signals representative of the sensed blood pressure when the second input is enabled; thereby generating signals representing the systolic blood pressure, the diastolic blood pressure, and blood pressures between the two as the deflating means is operative, as well as for indicating the cuff pressure during initial inflation of the cuff by the pressurizing means;
(K) a first display connected to the digital output signal of the A-D converter for generating a visual display of each output of the A-D converter and thereby maintaining the diastolic blood pressure reading upon termination of the threshold detector output signals;
(L) means, connected to the output of the threshold detector and energizable after initial cuff inflation, for generating the first control pulse and for generating at least a second control pulse when the threshold detector output is first generated after the first control pulse is generated;
(M) a second display for generating a digital output visual display of the systolic blood pressure; and
(N) means, connected to the output of the analog to digital converter, to the control means for sensing the second control pulse from the control means, and to the second display, for storing and driving the second display upon activation by the second control pulse;
whereby the first display shows the blood pressure in the cuff as the cuff is initially pressurized and also displays each blood pressure reading as the cuff pressure is reduced to and below the systolic pressure point, and latching the blood pressure reading upon receipt of the diastolic blood pressure; and wherein the second display shows the systolic blood pressure and maintains this reading until the unit is de-energized.

2. A blood pressure measurement device as defined in claim 1, wherein the pressurizing means is an air pump and wherein a first switch has a position to initially energize the device except for the control means, so that the threshold detector will generate an output pulse during pumping of the air pump and thereby display on the first display the pressure within the cuff as the cuff is being pressurized and wherein the control means is energized by a second switch which is activated after pressurization of the cuff exceeding an arterial occluding pressure so as to then initiate the sample and hold and compensation circuitry of the present invention.

3. A blood pressure measurement device as defined in claims 1 or 2, wherein the compensation means performs a reduction of the input signal to the amplifying means as a logarithmic function of the output amplitude of the amplifying means.

4. A blood pressure measurement device as defined in claim 3, wherein the compensation means reduction of the input signal to the amplifying means causes the output of the amplifying means to be less than the predetermined value of the threshold detector when the artery is totally occluded.

5. A blood pressure measurement device as defined in claims 1 or 2, wherein the means for generating control pulses generates a third control pulse after the second control pulse is generated and wherein the means for storing and driving the second display further has means for receipt of the third control pulse, and wherein the second control pulse causes the digital value from the A-D converter to be stored in the storing and driving means and wherein this stored value is used to drive the second display upon receipt of the third pulse.

6. A blood pressure measurement device as defined in claims 1 or 2, wherein the inflatable cuff is mounted on a band dimensioned to be worn about the wrist of the user.

7. A blood pressure measurement device as defined in claim 6, wherein the pressurizing means comprises an inflatable air bladder and wherein the activatable means for gradually deflating the pressurized cuff is a needle valve.

8. A blood pressure measurement device as defined in claim 6, wherein the band incorporates hook and loop area fastening means.

9. A blood pressure measurement device as defined in claim 1, wherein the transducer comprises a piezoelectric pressure sensor.

10. A method of measuring the blood pressure of a user comprising the steps of:
   (1) applying an external occluding pressure to a predetermined artery sufficient to temporarily stop the flow of blood;
   (2) gradually decreasing the externally applied pressure so as to gradually allow blood to flow through the artery in a partially occluded manner until a point of totally unoccluded blood flow is attained;
   (3) electrically sensing the applied pressure and the fluctuating pulse pressure caused either by the presence of a heart beat induced blood pressure variation during total occlusion of the artery or due to the presence of heart beat induced blood flowing through the artery;
   (4) electrically filtering the output of step 3 so as to pass only the fluctuating pulse pressure components;
   (5) electrically amplifying the fluctuating pulse pressure components;
   (6) logarithmically reducing the electrically amplified pulse pressure component after an external occluding pressure has been obtained so as to filter to a value less than a first predetermined value the amplified pulse pressure of the totally occluded artery;
   (7) enabling a detector output as the occluding pressure is applied to the predetermined artery and when the amplified fluctuating pulse pressure components are greater than the first predetermined value, which after initial arterial occlusion represents the systolic blood pressure occurrence, and disabling the detector output when the pressure component is less than this value, representing the diastolic blood pressure occurrence;
   (8) generating a digital electrical signal from the sensed applied pressure and fluctuating pulse pressure when the detector signal is first enabled as the occluding pressure is applied to the predetermined artery so as to originally represent the occluding pressure applied to the artery and later to represent the systolic blood pressure, and continuing to generate digital signals for each heart beat after the systolic blood pressure signal has been generated until the detector signal is disabled, at which point the diastolic blood pressure digital signal is generated; and
   (9) digitally displaying the digital electric signals representing initial occlusion of the artery, the systolic and diastolic blood pressures, and blood pressures between the systolic and diastolic pressures.

* * * * *